(12) United States Patent
Villa et al.

(10) Patent No.: US 7,692,025 B2
(45) Date of Patent: Apr. 6, 2010

(54) PROCESS FOR THE PREPARATION OF ANTICANCER DRUGS

(75) Inventors: Marco Villa, Milan (IT); Roberta Fretta, Collegno (IT); Nicola Diulgheroff, Turin (IT); Alessandro Pontiroli, Maria della Versa (IT)

(73) Assignee: Sicor, Inc., Irvine, CA (US)

( * ) Notice: Subject to any disclaimer, the term of this patent is extended or adjusted under 35 U.S.C. 154(b) by 815 days.

(21) Appl. No.: 11/400,639

(22) Filed: Apr. 6, 2006

(65) Prior Publication Data

US 2006/0276657 A1    Dec. 7, 2006

Related U.S. Application Data

(60) Provisional application No. 60/669,132, filed on Apr. 6, 2005, provisional application No. 60/694,528, filed on Jun. 27, 2005.

(51) Int. Cl.
*C07D 249/08* (2006.01)
(52) U.S. Cl. .................................... 548/262.2
(58) Field of Classification Search ................. 548/355, 548/262.2
See application file for complete search history.

(56) References Cited

U.S. PATENT DOCUMENTS

| 4,935,437 A * | 6/1990 | Edwards et al. ............. 514/383 |
| RE36,617 E | 3/2000 | Edwards et al. |
| 2006/0035950 A1 | 2/2006 | Alnabari et al. |
| 2006/0189670 A1 | 8/2006 | Khile et al. |
| 2006/0217569 A1 | 9/2006 | Schulze et al. |
| 2007/0100148 A1 | 5/2007 | Murki et al. |
| 2007/0281982 A1 | 12/2007 | Pis et al. |
| 2008/0076933 A1 | 3/2008 | Benes et al. |
| 2008/0177081 A1 | 7/2008 | Hsieh et al. |
| 2008/0207915 A1 | 8/2008 | Radhakrishnan et al. |

FOREIGN PATENT DOCUMENTS

| CA | 1337420 | 10/1995 |
| EP | 0 296 749 | 10/1994 |
| IL | 86499 A1 | 9/1997 |
| WO | WO-2005/089511 A2 | 9/2005 |
| WO | WO 2005/105762 | 11/2005 |
| WO | WO 2005/118560 | 12/2005 |
| WO | WO-2006/108155 A2 | 10/2006 |
| WO | WO-2007/002722 A2 | 1/2007 |
| WO | WO-2007/039919 A1 | 4/2007 |
| WO | WO-2007/054963 A2 | 5/2007 |
| WO | WO-2007/105231 A1 | 9/2007 |
| WO | WO-2007/134846 | 11/2007 |
| WO | WO-2007/141799 A1 | 12/2007 |
| WO | WO-2008/017781 A2 | 2/2008 |
| WO | WO-2008/034644 A2 | 3/2008 |
| WO | WO-2008/047104 A1 | 4/2008 |

OTHER PUBLICATIONS

Ge, Z., et al. "Improved Synthetic Method of Anticancer Drug Anastrozole" *Chinese Journal of Medicinal Chemistry*, vol. 13, No. 3, pp. 146-147, 152, (2003).

* cited by examiner

*Primary Examiner*—Golam M. M. Shameem
*Assistant Examiner*—Susannah Chung
(74) *Attorney, Agent, or Firm*—Kenyon & Kenyon LLP

(57) ABSTRACT

A process for preparing Anastrozole is provided. In the process the steps of a. combining 3,5-bis(2-cyanoisopropyl)toluene, a solvent selected from the group consisting of acetonitrile, dichloromethane and chlorobenzene, a brominating reagent selected from a group consisting of N-bromosuccinimide and 1,3-dibromo-5,5-dimethylhydantoin, and 2,2'-azobis(2-methylpropionitrile);
  b. heating;
  c. combining with 1,2,4-triazole, a solvent selected from a group consisting of N-methylpyrrolidinone, dimethylformamide, mixtures of NMP and DMF, dimethylsulfoxide, mixtures of DMSO and toluene, acetone, ACN, and tetrahydrofuran, a base selected from a group consisting of NaOH, KOH, $K_2CO_3$, and $Na_2CO_3$, and 1,3-benzendiacetonitrile-5-(bromomethyl)-α,α,α,α-tetramethyl, at a temperature below −20° C. are performed.

80 Claims, No Drawings

PROCESS FOR THE PREPARATION OF ANTICANCER DRUGS

RELATED APPLICATIONS

This application claims benefit of U.S. Provisional Patent Applications Nos. 60/669,132, filed Apr. 6, 2005, and 60/694,528, filed Jun. 27, 2005, the contents of which are incorporated herein in their entirety by reference.

FIELD OF THE INVENTION

The present invention is directed to a process for the preparation and purification of anticancer drugs. In particular, the invention is directed to a process for the preparation and purification of Anastrozole.

BACKGROUND OF THE INVENTION 1,3-benzenediacetonitrile-α,α,α',α'-tetramethyl-5-(1H-1,2,4-triazol-1-ylmethyl), 2,2'-[5-(1H-1,2,4-triazol-1-ylmethyl)-1,3-phenylene]bis(2-methylpropiononitrile), Anastrazole, of the formula,

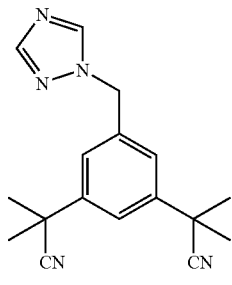
Anastrozole acts as an inhibitor of aromatase, and can be employed, either alone or in combination, for cancer therapy and prevention. Anastrozole, in particular, is widely accepted as highly effective, having only few undesirable side effects.

Preparation and purification of Anastrozole was first disclosed in EP 296,749, comprising a) the bromination of the toluene derivative, 3,5-bis(2-cyanoisopropyl)toluene, in carbon tetrachloride, producing a benzylic bromide, and b) the condensation of the resulting benzylic bromide in dimethylformamide with sodium 1,2,4-triazolyl according to the following scheme:

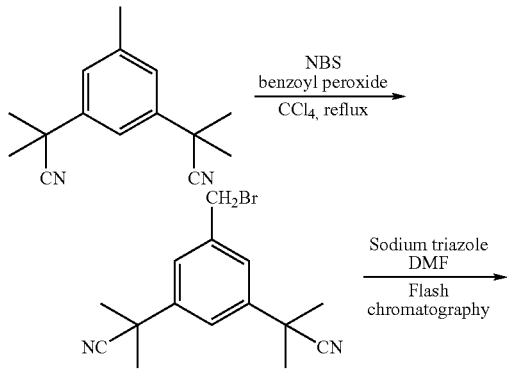

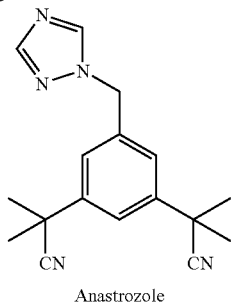
Anastrozole

The desired product is then obtained after a chromatographic separation.

SUMMARY OF THE INVENTION

In one aspect, the present invention provides a process for preparing Anastrozole of the following formula

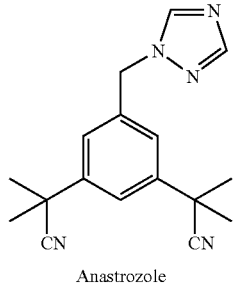
Anastrozole comprising combining 3,5-bis (2-cyanoisopropyl)toluene of formula I,

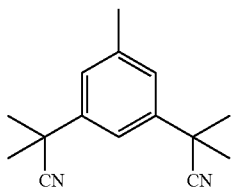

I a solvent selected from a group consisting of acetonitrile (referred to as ACN), dichloromethane (referred to as DCM) and chlorobenzene, a brominating reagent selected from a group consisting of N-bromosuccinimide (referred to as NBS) and 1,3-dibromo-5,5-dimethylhydantoin, and 2,2'-azobis(2-methylpropionitrile); heating; combining with 1,2,4-triazole, a solvent selected from a group consisting of N-methylpyrrolidinone (referred to as NMP), dimethylformamide (referred to as DMF), mixtures of NMP and DMF, dimethylsulfoxide (referred to as DMSO), mixtures of DMSO and toluene, acetone, ACN, and tetrahydrofuran (referred to as THF), a base selected from a group consisting of NaOH, KOH, $K_2CO_3$, and $Na_2CO_3$, and 1,3-benzendiacetonitrile-5-(bromomethyl)-α,α,α',α'-tetramethyl of formula II,

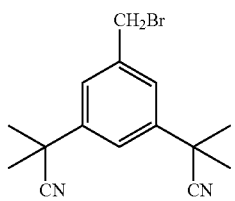

II at a temperature below −20° C.

In another aspect, the present invention provides a process a process for purifying Anastrozole comprising extracting with a mixture comprising of toluene, linear, branched or cyclic $C_{5-8}$ hydrocarbon and water; adding water; extracting the aqueous phase using toluene; extracting the organic phase with a polar mixture containing a solvent selected from a group consisting of NMP and $C_{1-3}$ alcohol mixed with water, and adding linear, branched or cyclic $C_{5-8}$ hydrocarbon to the organic phase to precipitate Anastrozole.

In yet another aspect, the present invention provides a process for preparing Anastrozole of the following formula

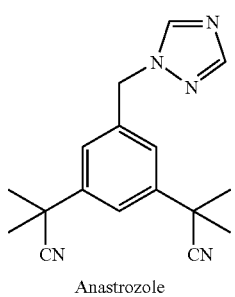

Anastrozole comprising combining 3,5-bis (2-cyanoisopropyl)toluene of formula I, a solvent selected from a group consisting of acetonitrile (referred to as ACN), dichloromethane (referred to as DCM) and chlorobenzene, a brominating reagent selected from a group consisting of N-bromosuccinimide (referred to as NBS) and 1,3-dibromo-5,5-dimethylhydantoin, and 2,2'-azobis(2-methylpropionitrile); heating; combining with 1,2,4-triazole, a solvent selected from a group consisting of: N-methylpyrrolidinone (referred to as NMP), dimethylformamide (referred to as DMF), mixtures of NMP and DMF, dimethylsulfoxide (referred to as DMSO), mixtures of DMSO and toluene, acetone, ACN, and tetrahydrofuran (referred to as THF), a base selected from a group consisting of NaOH, KOH, $K_2CO_3$, and $Na_2CO_3$, and 1,3-benzendiacetonitrile-5-(bromomethyl)-α,α,α,α-tetramethyl of formula II at a temperature below −20° C., and purifying by the purification process described herein above.

DETAILED DESCRIPTION OF THE INVENTION

The present invention relates to a process for preparing Anastrozole of the formula

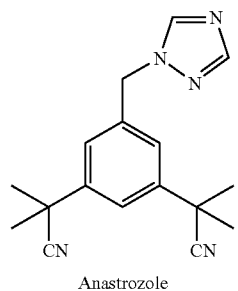

Anastrozole with high yield and purity, wherein the formation of isomeric products, such as Isoanastrozole of the formula,

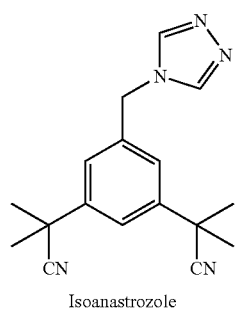

Isoanastrozole is minimized under the reaction conditions, i.e., the reaction is selective. In addition, the present invention also relates to a process for purifying Anastrozole from Isoanastrozole and from other impurities by selective extraction of the Anastrozole by the utilization of carefully chosen solvents and/or mixtures of solvents. Also, this process does not require the isolation of Anastrozole in a form of a salt, thus, the steps of transforming Anastrozole to its salt and then back to the free base are avoided. Hence, the process of the present invention can be adapted easily and efficiently to industrial scale, as compared to the processes of the prior-art, wherein toxic solvents, such as carbon tetra-chloride, and column chromatography are used. Since a highly pure form, typically greater than 99.5 percent, of any drug is generally required for human treatment, a method that combines the control of the formation of isomers and a facile final purification is particularly advantageous.

The present invention provides a process for preparing Anastrozole of the following formula

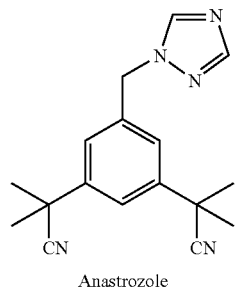

Anastrozole comprising combining 3,5-bis (2-cyanoisopropyl)toluene of formula I,

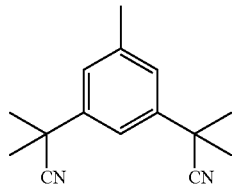

I a solvent selected from a group consisting of acetonitrile (referred to as ACN), dichloromethane (referred to as DCM) and chlorobenzene, a brominating reagent selected from a group consisting of N-bromosuccinimide (referred to as NBS) and 1,3-dibromo-5,5-dimethylhydantoin, and 2,2'-azo-bis(2-methylpropionitrile); heating; combining with 1,2,4-triazole, a solvent selected from a group consisting of N-methylpyrrolidinone (referred to as NMP), dimethylformamide (referred to as DMF), mixtures of NMP and DMF, dimethylsulfoxide (referred to as DMSO), mixtures of DMSO and toluene, acetone, ACN, and tetrahydrofuran (referred to as THF), a base selected from a group consisting of NaOH, KOH, K₂CO₃, and Na₂CO₃, and 1,3-benzendiacetonitrile-5-(bromomethyl)-α,α,α,α-tetramethyl of formula II

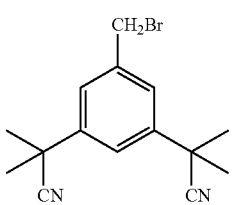

II at a temperature below −20° C.

The process for preparing Anastrozole may be illustrated by the following Scheme;

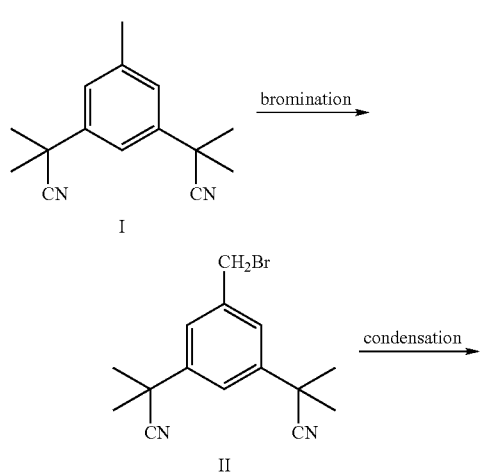

wherein any derivative of 1,3-benzendiacetonitrile-5-(bromomethyl)-α,α,α,α-tetramethyl of formula II, containing a leaving group different from bromine can be used. Preferably, the derivative may contain a leaving group selected from a group consisting of Cl, I, methylsulfonate, and toluenesulfonate. More preferably, 1,3-benzendiacetonitrile-5-(bromomethyl)-α,α,α,α-tetramethyl of formula II is used in the synthesis of Anastrozole.

Preferably, the bromination may be carried out by dissolving 3,5-bis (2-cyanoisopropyl)toluene of formula I in a solvent selected from a group consisting of ACN, DCM and chlorobenzene, followed by adding a brominating reagent selected from a group consisting of NBS and 1,3-dibromo-5,5-dimethylhydantoin to obtain a suspension. The suspension is then maintained at a temperature of about 20° C. to about 90° C. to obtain a solution, which is then combined with 2,2'-azobis(2-methylpropionitrile), providing a reaction mixture. The reaction mixture is heated to a temperature of about 40° C. to about 95° C., for about 6 to about 12 hours, providing 1,3-benzendiacetonitrile-5-(bromomethyl)-α,α,α,α-tetramethyl of formula II.

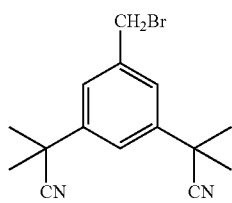

II 3,5-bis (2-cyanoisopropyl)toluene of formula I used as a starting material for the bromination reaction is commercial.

The preferred brominating reagent is NBS. The preferred solvent for the bromination is ACN. Preferably, the suspension is maintained at a temperature of about 65° C. to about 82° C., when ACN is used, and at a temperature of about 20° C. to about 30° C., more preferably, at a temperature of about 25° C. to about 30° C., when DCM is used. Preferably, the suspension is maintained at a temperature of about 80° C. to about 95° C., when chlorobenzene is used as a solvent. Preferably, the suspension is maintained for about 30 minutes to about an hour, more preferably, for about 30 to about 40 minutes, to obtain a solution, prior to combining with 2,2'-azobis(2-methylpropionitrile). Preferably, the reaction mixture is heated to a temperature of about 70° C. to about 82° C. Preferably, the reaction mixture is heated to for about 6 to about 10 hours.

1,3-benzendiacetonitrile-5-(bromomethyl)-α,α,α,α-tetramethyl of formula II may be recovered by allowing the reaction mixture to cool to a temperature of about 25° C. to about 20° C., followed by adding an aqueous solution of

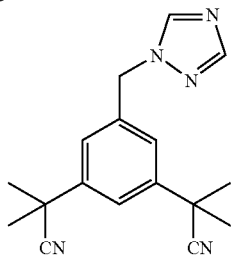

sodium metabisulphite and stirring. Then, a solvent selected from a group consisting of toluene, xylene and ethylacetate is added, and stirring is continued for about 30 to about 60 minutes, followed by separating the phases and concentrating the organic phase.

1,3-benzendiacetonitrile-5-(bromomethyl)-α,α,α,α-tetramethyl of formula II may be purified by concentrating the organic phase, to obtain a slurry, which is heated to a temperature of about 50° C. to about 55° C., to obtain a solution. Subsequently, a solvent selected from a group consisting of heptane, hexane, methylhexane, cyclohexane and isooctane, is added over a period of about 30 minutes to about 45 minutes, and cooling to a temperature of about 25° C. to about 10° C. is then performed, and the product is collected, preferably, by filtration and drying.

Preferably, the condensation may be performed by dissolving 1,2,4-triazole in a first solvent selected from a group consisting of NMP, DMF, mixtures of NMP and DMF, DMSO, mixtures of DMSO and toluene, acetone, ACN, and THF, at a temperature of about 20° C. to about 65° C., followed by a portion-wise addition of a base selected from a group consisting of NaOH, KOH, $K_2CO_3$, and $Na_2CO_3$, while maintaining the temperature below 65° C., thus providing a solution. The solution is then maintained for about 6 to about 18 hours, and then cooled to a temperature below –20° C. A solution of 1,3-benzendiacetonitrile-5-(bromomethyl)-α,α,α,α-tetramethyl of formula II or of any of the other derivatives of the compound of formula II containing a leaving group different from bromine in a second solvent, listed above, is then added slowly, while maintaining the temperature below –20° C. At the end of the addition, the reaction is maintained at the same temperature for about 10 to about 20 hours, and then it is quenched.

Preferably, 1,2,4-triazole is dissolved in the first solvent at a temperature of about 20° C. to about 35° C., more preferably, at a temperature of about 20° C. to about 25° C. Preferably, the first solvent is NMP. Preferably, the base is NaOH. Optionally, a salt, such as, $Na_2SO_4$ may be added after the base is added. Preferably, the base is added over a period of about one to about one and half hours. While the base is added, the temperature is maintained, preferably, at about 30° C. to about 60° C., more preferably, at about 30° C. to about 35° C., providing a solution. The solution is, preferably, maintained for about 16 to about 20 hours. The solution is, preferably, cooled to a temperature of about –20° C. to about –30° C., more preferably, to a temperature of about –20° C. to about –25° C., prior to the addition of 1,3-benzendiacetonitrile-5-(bromomethyl)-α,α,α,α-tetramethyl of formula II, or of any of the other derivatives of the compound of formula II containing a leaving group different from bromine. This temperature is also maintained during the addition of the solution of compound of formula II. 1,3-benzendiacetonitrile-5-(bromomethyl)-α,α,α,α-tetramethyl of formula II used in the condensation reaction may be the crude obtained from the bromination reaction without further purification. Moreover, under the reaction conditions the impurities contained in crude 1,3-benzendiacetonitrile-5-(bromomethyl)-α,α,α,α-tetramethyl of formula II do not react. Preferably, the second solvent may be the same as the first solvent. Preferably, the solution of 1,3-benzendiacetonitrile-5-(bromomethyl)-α,α,α,α-tetramethyl of formula II or of any of the other derivatives of the compound of formula II containing a leaving group different from bromine in a second solvent is added over a period of about 4 to about 10 hours, more preferably, over a period of about 5 to about 7 hours. After the addition, the reaction is maintained, preferably, for about 16 to about 20 hours. Maintaining the reaction is done, preferably, at a temperature of less than –20° C., more preferably, at a temperature of about –20° C. to about –30° C., and even more preferably, at a temperature of about –20° C. to about –25° C. The progress of the reaction, after the addition of the solution of 1,3-benzendiacetonitrile-5-(bromomethyl)-α,α,α,α-tetramethyl of formula II or of any of the other derivatives of the compound of formula II containing a leaving group different from bromine, may be monitored by HPLC. Preferably, quenching may be done by using an organic acid in an amount sufficient to obtain a pH of about 6.5 to about 7. Preferably, the organic acid is acetic acid.

Preferably, Anastrozole may be purified comprising extracting the quenched reaction mixture with a mixture comprising of toluene, linear, branched or cyclic $C_{5-8}$ hydrocarbon, and water; adding water; extracting the aqueous phase using toluene; extracting the organic phase with a polar mixture containing a solvent selected from a group consisting of NMP and $C_{1-3}$ alcohol mixed with water, and adding linear, branched or cyclic $C_{5-8}$ hydrocarbon to the organic phase to precipitate Anastrozole.

The extractions are selective due to the difference in the solubility of the non-polar impurities, vs. Anastrozole and vs. the more polar Isoanastrozole. Preferably, the addition of toluene, linear, branched, or cyclic $C_{5-8}$ hydrocarbon and water to the quenched reaction provides a biphasic mixture that allows the non-polar impurities to separate from Anastrozole by dissolving them in the organic phase, while Anastrozole is dissolved in the aqueous phase. The layers are then separated, and then Anastrozole is placed back into the organic phase by adding water and extracting the aqueous phase using toluene. The phases are separated again, and the organic phase is extracted with a polar mixture containing a solvent selected from a group consisting of NMP and $C_{1-3}$ alcohol mixed with water, thus, assuring that Isoanastrozole is extracted into in the aqueous phase, while Anastrazole remains in the organic phase.

Optionally, Anastrozole may be purified in a process comprising extracting the quenched reaction mixture with a mixture of toluene, linear, branched or cyclic $C_{5-8}$ hydrocarbon and water; extracting the aqueous phase using a mixture of toluene and linear, branched or cyclic $C_{5-8}$ hydrocarbon; adding water; extracting the aqueous phase using toluene; washing the organic phase with an aqueous solution of an acid; adding linear, branched or cyclic $C_{5-8}$ hydrocarbon to the organic phase to precipitate Anastrozole.

Preferably, prior to the extraction of the aqueous phase using toluene, an extraction of the aqueous phase using a mixture of toluene, linear, branched or cyclic $C_{5-8}$ hydrocarbon and water, may be done. Optionally, an aqueous solution of NaCl may be used instead of water. Preferably, in the process wherein an acid is applied, the aqueous phase is extracted by adding toluene and an aqueous solution of NaCl, thus providing an organic phase, which can be washed with an aqueous solution of NaCl, prior to washing with an acid. The addition of an aqueous solution of an acid ensures that Isoanastrozole is removed completely by transforming it, selectively, to its salt, hence extracting it into the aqueous phase, while Anastrozole remains in the organic phase. Preferably, the acid may be an organic acid or an inorganic acid. A preferred organic acid is either tartaric or citric acid. A preferred inorganic acid is either sulfuric acid or HCl.

Preferably, prior to adding linear, branched, or cyclic $C_{5-8}$ hydrocarbon to precipitate Anastrozole, the organic phase is concentrated, preferably, under reduced pressure. Preferably, the linear, branched, or cyclic $C_{5-8}$ hydrocarbon is added drop-wise to the concentrated organic phase. More preferably, the addition is done over a period of about 1 to about 1.5 hours, providing a suspension. The suspension is then cooled to a temperature of about 10° C. to about 0° C., preferably, to about 5° C. to about 0° C., and the precipitate is collected, preferably, by filtration, and dried.

Preferably, the linear, branched or cyclic $C_{5-8}$ hydrocarbon may be hexane, heptane or cyclohexane, more preferably, heptane. Preferably, the $C_{1-3}$ alcohol is methanol. Preferably, the polar mixture contains methanol and water.

Anastrozole may be further purified by crystallization from a mixture of a solvent and an anti-solvent; wherein the solvent is selected from a group consisting of acetone, ethanol, 2-propanol, methanol, DCM, n-butanol, ACN, ethylacetate, and toluene, and the anti-solvent is selected from a group consisting of heptane, diisopropylether (referred to as DIPE), water, and cyclohexane. The preferred mixtures are that of acetone and heptane, ethanol and heptane, ethanol and DIPE, ethanol and water, methanol and water, DCM and DIPE, 2-propanol and heptane, n-butanol and heptane, 2-propanol and DIPE, 2-propanol and water, n-butanol and DIPE, ACN and water, 2-propanol and heptane, and toluene and heptane. The more preferred mixtures are that of 2-propanol and heptane, toluene and heptane, and methanol and water.

Preferably, the crystallization is done by dissolving Anastrozole in the solvent, followed by a drop-wise addition of the anti-solvent, and cooling to a temperature of about 10° C. to about 0° C. The Anastrozole purified by crystallization may be crude Anastrozole. Crude Anastrozole may contain at least one of the impurities: Isoanastrozole, 3,5-bis(2-cyanoisopropyl)toluene, 1,1-dibromomethyl-3,5-bis(2-cyanoisopropyl)benzene and other impurities. Preferably, dissolution is done by heating Anastrozole and the solvent to a temperature of about 20° C. to about 55° C. When the solvent is methanol, the preferred temperature range is of about 20° C. to about 30° C., more preferably, of about 20° C. to about 25° C., and when the solvent is either 2-propanol or toluene, the preferred range is of about 40° C. to about 50° C. Preferably, the anti-solvent is added slowly, more preferably, over a period of about 15 minutes to about 2 hours. When the solvent is 2-propanol or toluene, and, the anti-solvent is heptane, the addition is done, preferably, over a period of about 0.5 an hour to about 2 hours, and even more preferably, over a period of about an hour to about 1.2 hours. When the solvent is methanol and the anti-solvent is water the addition is done, preferably, over a period of about 1 hour to about 2 hours, and even more preferably, over a period of about 75 to about 100 minutes. Preferably, the anti-solvent is added under stirring. At the end of the addition a suspension may be obtained. Preferably, the suspension is cooled to a temperature of about 5° C. to about 0° C., more preferably, to a temperature of about 2° C. to about 0° C. Cooling may be done over a period of about 1 to about 2 hours, preferably, over a period of about 75 to about 100 minutes. Preferably, after reaching a temperature of about 10° C. to about 0° C., the suspension is further maintained for about 1 hour to about 2 hours, more preferably, for about 1.5 to about 2 hours, and even more preferably, for about 90 to about 100 minutes. Purified Anastrozole may be recovered by filtering off the precipitate and drying, preferably under reduced pressure, at a temperature of about 55° C. Anastrozole obtained by the described purification process may have a purity of at least 99.5%% area by HPLC, more preferably, of at least 99.6%, and even more preferably, of at least 99.7% area by HPLC. Anastrazole obtained by the described purification process may contain at least on of the following impurities: not more than about 0.16% area by HPLC of Isoanastrazole, not more than about 0.14% area by HPLC of 3,5-bis (2-cyanoisopropyl)toluene, and not more than about 0.18% area by HPLC of other impurities.

The present invention provides, in addition, a process for purifying Anastrozole comprising extracting with a mixture comprising of toluene, linear, branched or cyclic $C_{5-8}$ hydrocarbon and water; extracting the aqueous phase using a mixture of toluene and water; extracting the organic phase with a polar mixture containing a solvent selected from a group consisting of NMP and $C_{1-3}$ alcohol mixed with water, and adding linear, branched or cyclic $C_{5-8}$ hydrocarbon to the organic phase to precipitate Anastrozole.

The present invention also provides a process for preparing Anastrozole of the following formula

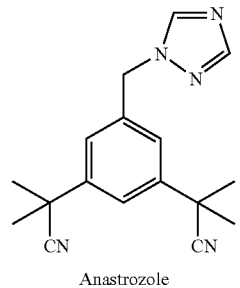

Anastrozole comprising combining 3,5-bis (2-cyanoisopropyl)toluene of formula I, a solvent selected from a group consisting of acetonitrile (referred to as ACN), dichloromethane (referred to as DCM) and chlorobenzene, a brominating reagent selected from a group consisting of N-bromosuccinimide (referred to as NBS) and 1,3-dibromo-5,5-dimethylhydantoin, and 2,2'-azobis(2-methylpropionitrile); heating; combining with 1,2,4-triazole, a solvent selected from a group consisting of: N-methylpyrrolidinone (referred to as NMP), dimethylformamide (referred to as DMF), mixtures of NMP and DMF, dimethylsulfoxide (referred to as DMSO), mixtures of DMSO and toluene, acetone, ACN, and tetrahydrofuran (referred to as THF), a base selected from a group consisting of NaOH, KOH, $K_2CO_3$, and $Na_2CO_3$, and 1,3-benzendiacetonitrile-5-(bromomethyl)-α,α,α,α-tetramethyl of formula II at a temperature below −20° C., and purifying by the purification process described herein above.

Monitoring the progress of the reaction as well as determining the purity of Anastrozole is done according to the HPLC method comprising the following steps: combining a sample of Anastrozole or of the reaction mixture with acetonitrile, to obtain a solution. The obtained solution is then injected into a 100×4.6 mm Hypersil BDS C18 (or similar) column, followed by eluting the sample from the column at about 35 min using a mixture of water (referred to as eluent A) and acetonitrile (referred to as eluent B) as an eluent, and measuring the content of Anastrozole in the relevant sample with a UV detector. (preferably at a 210 nm wavelength).

The eluent used may be mixture of eluent A and eluent B, wherein the ratio of them varies over the time, i.e. a gradient eluent. At the time 0 minutes, the eluent contains 80% of eluent A and 20% of eluent B. At 30 minutes, the eluent contains 40% of eluent A and 60% of eluent B. At 35 minutes, the eluent contains 20% of eluent A and 80% of eluent B, and at 36 minutes, the eluent contains 80% of eluent A and 20% of eluent B.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention. DSC thermogram and XRD spectrum of final compound are also provided for complete characterisation of the final material.

EXAMPLES

HPLC Method for Monitoring the Reaction and Purity of Final Material:

| Column & Packing: | HYPERSIL BDS C18; 3 µm, 100 mm × 4.6 mm, cat n. 28103-104630 or equivalent |
|---|---|
| Eluent A: | Water |
| Eluent B: | Acetonitrile |

| | Gradient | |
|---|---|---|
| Time (min) | % Eluent A | % Eluent B |
| 0 | 80 | 20 |
| 30 | 40 | 60 |
| 35 | 20 | 80 |
| 36 | 80 | 20 |

| Stop time | 35 minutes |
|---|---|
| Equilibrium time: | 5 minutes |
| Flow Rate: | 1.0 mL/mins. |
| Detector: | UV at 210 nm |
| Column temperature: | 60° C. |
| Injection | 5 µl |
| Diluent | Acetonitrile |

Mobile phase composition and flow rate may be varied in order to achieve the required system suitability.

Example 1

Synthesis of 1-bromomethyl-3,5-bis (2-cyanoisopropyl)toluene in ACN

Fifty grams of 3,5-bis (2-cyanoisopropyl)toluene was dissolved in 350 ml of acetonitrile, and 41.1 g of N-bromosuccinimide was added. The resulting suspension was heated to 50° C. for 30 minutes, until completely dissolved. Then, 0.5 g of 2,2'-azobis(2-methylpropionitrile) was added, and the reaction was heated to 70° C. for about 8 hours. The solution was then allowed to cool to about 20° C., and 350 ml of a 5 percent by weight solution of sodium metabisulphite in water was added in 30 min under vigorous stirring. Toluene was then added in an amount of 350 ml, and the biphasic system was stirred for 30 minutes. The organic layer was separated and washed with 200 ml of water containing 5 percent by weight sodium carbonate before removal of the organic solvent under reduced pressure, until a total volume of 120 ml was achieved.

The slurry thus obtained was then heated to 50° C., and 350 ml of heptane was slowly added over a period of 30 minutes, rising the temperature to 70° C. The suspension was then allowed to cool to 20° C., and was filtered on a sintered glass funnel. Drying under reduced pressure yielded 54 g of crude 1-bromomethyl-3,5-bis (2-cyanoisopropyl)toluene in 85 percent purity, based on HPLC area percent.

$^1$H NMR data for 1-bromo-3,5-bis (2-cyanoisopropyl) toluene: δ (ppm): 7.48-7.44 (m, 3H; phenyl ring H); 4.50 (s, 2H, CH$_2$Br); 1.75 (s, 6H, isopropyl CH$_3$).

Example 2

Synthesis of 1-bromomethyl-3,5-bis (2-cyanoisopropyl)toluene in DCM

First, 1.13 g of 3,5-bis (2-cyanoisopropyl)toluene was dissolved in 7.5 ml of dichloromethane, and 0.94 g of N-bromosuccinimide was added. The resulting suspension was stirred at 20° C. for 30 minutes, until complete dissolution was achieved. Then, 16 mg of 2,2'-azobis(2-methylpropionitrile) is added, and the reaction was heated to 40° C. for about 8 hours. The solution was then allowed to cool to 20° C., and poured into 10 ml of a 5 percent by weight solution of sodium metabisulphite in water with vigorous stirring. Toluene in an amount of 7.5 ml was then added, and the biphasic system was stirred for 30 minutes. The organic layer was separated, and the organic solvent was removed until final volume of 2 ml is obtained. 10 ml of heptane was slowly added over a period of 30 minutes, rising the temperature to 70° C. The suspension was then allowed to cool to 20° C., and was filtered on a sintered glass funnel. Drying under reduced pressure yields 1.5 g of crude 1,3-benzenediacetonitrile-5-(bromomethyl)-α,α,α,α tetramethyl in 80 percent purity, based on HPLC area percent.

Example 3

Synthesis of 1-bromomethyl-3,5-bis (2-cyanoisopropyl)toluene in ACN

First, 0.3 g of 3,5-bis (2-cyanoisopropyl)toluene was dissolved in 7 ml of acetonitrile, and 0.1 g of 1,3-dibromo-5,5-dimethylhydantoin is added. The suspension was then stirred at 20° C. for 30 minutes, until complete dissolution was achieved. Then, 4 mg of 2,2'-azobis(2-methylpropionitrile) was added, and the reaction was heated to 70° C. for 8 hours. The solution was then allowed to cool to 20° C., and poured into 7 ml of a 5 percent by weight solution of sodium metabisulphite in water with vigorous stirring. Toluene (7.5 ml) was then added, and the biphasic system was stirred for 30 minutes. The organic layer was separated and the organic solvent was removed until final volume of 1 ml is obtained. Then, the solution was heated to 50° C., and 10 ml of heptane was slowly added over a period of 30 minutes, rising the temperature to 70° C. The suspension was then allowed to cool to 20° C., and was filtered on a sintered glass funnel. Drying under reduced pressure yielded 0.3 g of crude 1,3-benzenediacetonitrile-5-(bromomethyl)-α,α,α,α tetramethyl in 86 percent purity, based on HPLC area percent.

Example 4

Synthesis of 1-bromomethyl-3,5-bis (2-cyanoisopropyl)toluene in chlorobenzene 10 g of 3,5-bis (2-cyanoisopropyl)toluene were dissolved in 48 ml of chlorobenzene, and 8.26 g of N-bromosuccinimide was added. The suspension was then stirred at 90° C. for 30 minutes. Then, 4 mg of 2,2'-azobis(2-methylpropionitrile) were added and a complete dissolution was achieved, and the reaction was heated to 95° C. for 8 hours. The solution was then allowed to cool to 20° C., and poured into 50 ml of a 5 percent by weight solution of sodium metabisulphite in water with vigorous stirring. Toluene (20 ml) was then added, and the biphasic system was stirred for 30 minutes. The organic layer was separated and the organic solvent was removed. Toluene (22 ml) was added and the slurry was heated to 50° C., and 10 ml of heptane was slowly added over a period of 30 minutes, rising the temperature to 70° C. The suspension was then allowed to cool to 20° C., and was filtered on a sintered glass funnel. Drying under reduced pressure yielded 4 g of crude 1,3-benzenediacetonitrile-5-(bromomethyl)-α,α,α,α tetramethyl in 86 percent purity, based on HPLC area percent.

Example 5

Synthesis of Anastrozole

First, 144.7 g of 1,2,4-triazole were dissolved in 1900 ml of NMP at 20° C., and 84 g of NaOH were added in portions over 1 hour, while maintaining the temperature at less than 35° C. The solution was stirred for 18 hours at 20° C., and then cooled to −22° C. A solution of 355 g of crude 1,3-benzene-diacetonitrile-5-(bromomethyl)-α,α,α,α tetramethyl (having a purity of 85.6%, containing: 3,5-bis(2-cyanoisopropyl) toluene 5.5%, 1,1-dibromo-3,5-bis(2-cyanoisopropyl)toluene 7.83%, and other impurities 3.5%) in 800 ml of NMP was slowly added over 6 hours, while maintaining the temperature below −20° C.

At the end of the addition, the suspension was stirred for 18 hours at −20° C., during which the reaction was monitored via HPLC. When the amount of starting material was less than 0.5 percent, acetic acid was added in an amount sufficient to provide a pH of about 6.5 to about 7. (An HPLC analysis of the crude reaction mixture showed: residual starting material 0.44%, Anastrozole 78.7%, Isoanastrozole 5.5%, 3,5-bis (2-cyanoisopropyl)toluene 11.6%, 1,1-dibromomethyl-3,5-bis(2-cyanoisopropyl)benzene 3.5%, and 0.3% other impurities.) The mixture was slowly allowed to warm to 20° C., then 1 l of toluene, 2 l of heptane, and 1700 ml of water were added. The biphasic system was stirred vigorously for 30 minutes, and the organic layer was then separated. Water in an amount of 1100 ml, 760 ml of toluene, and 1500 ml of heptane were added to the aqueous phase, and the system was stirred for 30 minutes before the organic phase was separated. Then 2.5 l of toluene and 10 l of water were added to the aqueous portion, and the biphasic system was stirred for 1 hour. The organic layer was separated and washed three times with a mixture of 300 ml of MeOH and 2100 ml of water. The final organic phase was concentrated under reduced pressure to a final volume of 1500 ml at 40° C., and 1500 ml of heptane was added dropwise over a period of 1 hour. The suspension was cooled to 0° C., stirred for 1 hour, and filtered. The crude solid was dissolved in 1000 ml of 2-propanol at 50° C., and 400 ml of heptane was slowly added under stirring.

The solution was cooled to 0° C., stirred for 1 hour, and filtered. The solid was dried at 55° C. under reduced pressure until constant weight was achieved, producing 204 g of product with a purity as follows: Anastrozole 99.75%, Isoanastrozole 0.05%, 3,5-bis (2-cyanoisopropyl)toluene 0.06%, other impurities 0.13% area by HPLC, and with a melting point of 85° C., measured by DSC.

$^1$H NMR data for anastrozole (CDCl$_3$, 297K): δ (ppm): 8.15 (s, 1H; triazole C$_3$H); 7.91 (s, 1H, triazole Cl H); 7.47 (t, 1H, phenyl C$_4$H); 7.27 (d, 2H, phenyl C$_{2-6}$H); 5.34 (s, 2H, benzylic CH$_2$); 1.64 (s, 12H, CH$_3$).

Example 6

Synthesis of Anastrozole

First, 3.8 g of 1,2,4-triazole were dissolved in 8 ml of NMP at 20° C. Then, 2.2 g of NaOH and 22 ml of NMP were added in portions over 1 hour, maintaining the temperature at less than 35° C. The solution was stirred for 2 hours at 20° C., and 7.8 g of Na$_2$SO$_4$ were then added. After filtration of the solid, the resulting solution was transferred to a dropping funnel, and added over 75 minutes to a solution of 14 g of crude 1,3-benzenediacetonitrile-5-(bromomethyl)-α,α,α,α tetramethyl (having a purity of 81.8%, containing: 3,5-bis(2-cyanoisopropyl)toluene 4.0%, 1,1-dibromo-3,5-bis(2-cyanoisopropyl)toluene 10.7%, and other impurities 3.5%) in 20 ml of NMP, cooled to −30° C. At the end of the addition, the suspension was stirred at −30° C. for 18 hours, and monitored via HPLC. When the concentration of starting material is less than 0.5 percent, an amount of acetic acid sufficient to give a pH of about 6.5 to about 7.0 is added (an HPLC analysis of the crude reaction mixture showed: residual starting material 0.4%, Anastrozole 68.9%, Isoanastrozole 5.5%, 3,5-bis (2-cyanoisopropyl)toluene 7.5%, 1,1-dibromomethyl-3,5-bis(2-cyanoisopropyl)benzene, and 15.4%, and other impurities 2.3%.). The mixture is then allowed to warm slowly to 20° C., filtered, and 37 ml of toluene, 75 ml of heptane, and 37 ml of water are added. The biphasic system is stirred vigorously for 30 minutes, and the organic layer is then separated. Water, toluene, and heptane in amounts of 25 ml, 25 ml, and 50 ml, respectively, are added to the aqueous phase, and the system is stirred for 30 minutes before the organic phase is separated. Then, 10 ml of toluene and 20 ml of heptane are added to the aqueous phase, and the system is stirred for 30 minutes before the organic phase is separated. Toluene and water, 99 ml and 400 ml, respectively, are added to the aqueous phase, and the resulting biphasic system is stirred for 1 hour. The organic layer is separated and washed 3 times with a mixture of MeOH and water (3 ml and 21 ml, respectively). The final organic phase is concentrated to 45 ml under reduced pressure at 40° C., and 45 ml of heptane are added dropwise over 1 hour. The resulting suspension is cooled to 0° C., stirred for 1 hour, and filtered. The crude solid is dissolved in toluene (40 ml) at 40° C., and heptane (40 ml) is slowly added under stirring. The suspension is cooled to 0° C., stirred for 1 hour, and filtered. The solid is dried at 55° C. under reduced pressure until constant weight is achieved, yielding 5.8 g of product with a purity as follows: Anastrozole 98.45%, Isoanastrozole 0.09%, 3,5-bis (2-cyanoisopropyl)toluene 0.06%, 1-bromo-3,5-bis (2-cyanoisopropyl)toluene 0.11%, 1,1-dibromo-3,5-bis(2-cyanoisopropyl)toluene 0.07%, other impurities 1.22% are by HPLC.

Example 7

Synthesis of Anastrozole (Alternative Work-up)

First, 14.9 g of 1,2,4-triazole were dissolved in 40 ml of NMP at 20° C., and 8.64 g of NaOH in 180 ml of NMP were added, while maintaining the temperature at less than 35° C. The mixture was stirred for 55 hours at 20° C., and then cooled to −26° C. A solution of 37 g of crude 1,3-benzenediacetonitrile-5-(bromomethyl)-α,α,α,α tetramethyl in 73 ml of NMP was added over 6 hours. At the end of the addition, the suspension was stirred for 20 hours at −26° C., and the reaction was monitored with HPLC. When the concentration of starting material was less than 0.5 percent, an amount of acetic acid sufficient to give a pH of about 6.5 to about 7 was added. The mixture was allowed to warm slowly to 20° C., and 135 ml of toluene, 270 ml of heptane, and 194 ml of water were added. The biphasic system was stirred vigorously for 30 minutes, and the organic layer was separated. Then 140 ml of toluene and 270 ml of heptane were added to the aqueous phase obtained above, and the system was stirred for 30 minutes, the organic phase was separated, and 100 ml of water, 70 ml of toluene, and 135 ml of heptane were added to the aqueous phase obtained above. The system was then stirred for 30 minutes, and the organic phase was separated. Water in an amount of 1750 ml was added to the aqueous phase, and the product was extracted with toluene 4 times with a total volume of toluene of 530 ml. The organic phases were combined and washed with 130 ml of a 10 percent by weight solution of tartaric acid 2 times. The final organic phase was concentrated to 154 ml under reduced pressure at 40° C., and 155 ml of heptane were added dropwise over 1 hour. The suspension was cooled to 0° C., stirred for 1 hour, and filtered. The crude solid obtained can be crystallized as described in example 5.

Example 8

Synthesis of Anastrozole

First, 14.9 g of 1,2,4-triazole were dissolved in 40 ml of NMP at 20° C., and 8.64 g NaOH in 180 ml of NMP were added, while maintaining the temperature at less than 35° C. The mixture was stirred for 55 hours at 20° C., and then cooled to −26° C. A solution of 37 g of crude 1,3-benzenediacetonitrile-5-(bromomethyl)-α,α,α,α tetramethyl in 73 ml of NMP, cooled to −26° C., was added over a period of 6 hours. At the end of the addition, the suspension was stirred for 20 hours at −26° C., and the reaction is monitored with HPLC. When the starting material was at a concentration of less than 0.5 percent, an amount of acetic acid sufficient to give a pH of about 6.5 to about 7 was added. The mixture was allowed to warm slowly to 20° C., and 135 ml of toluene, 270 ml of heptane, and 195 ml of water were added. The biphasic system was stirred vigorously for 30 minutes, and the organic layer was separated. Then, 140 ml of toluene and 275 ml of heptane were added to the aqueous phase obtained above, the system was stirred for 30 minutes, and the organic phase was separated. After the separation, 100 ml of water, 70 ml of toluene, and 135 ml of heptane were added to the aqueous phase obtained above, the system was stirred for 30 minutes, and the organic phase was separated. Then, 1750 ml of water were added to the aqueous phase, and the product was extracted with toluene 4 times. The organic phases were combined and washed two times with 130 ml of a solution of HCl having a pH of 1.4. The final organic phase was concentrated to 154 ml under reduced pressure at 40° C., and 154 ml of heptane was added dropwise over a period of 1 hour. The suspension was cooled to 0° C., stirred for 1 hour, and filtered. The crude solid can be crystallized as in example 5.

Example 9

Crystallization of Anastrozole

First, 14.6 g of crude Anastrozole, obtained as in example 5 from toluene/heptane, were dissolved in 80 ml of methanol at 20° C., and 5 ml of water were added dropwise. Then the mixture was stirred at 20° C. for 20 minutes. 160 ml of water were added dropwise over 90 min at 20° C. The slurry was cooled to 0° C. in 90 minutes, and maintained at the same temperature for 90 minutes. The solid was filtered and washed with 120 ml of water and then the solid was dried at 55° C. under vacuum for 16 hours, yielding 11.20 g of product having HPLC purity as follows: Anastrozole 99.52%, Isoanastrozole 0.16%, 3,5-bis (2-cyanoisopropyl)toluene 0.14%, and other impurities 0.18.

Example 10

Synthesis of Anastrozole

First, 17.1 g of 1,2,4-triazole were dissolved in 52 ml of NMP at 20° C., and 9.72 g NaOH in 104 ml of NMP were added, while maintaining the temperature at about 60° C. The mixture was stirred for 2 hours at 60° C., was cooled and stirred for at least 12 hours at 22° C. and was then cooled to −25° C. A solution of 40 g of crude 1,3-benzenediacetonitrile-5-(bromomethyl)-α,α,α,α tetramethyl in 78 ml of NMP was added at −25° C. over a period of 5-6 hours. At the end of the addition, the suspension was stirred for 18 hours at −25° C., and the reaction was monitored with HPLC. When the starting material was at a concentration of less than 0.5 percent, an amount of acetic acid sufficient to give a pH of about 6.5 to about 7 was added. The mixture was allowed to warm slowly to 20° C., and 120 ml of toluene, 240 ml of heptane, and 168 ml of water were added. The biphasic system was stirred vigorously for 30 minutes, and the organic layer was separated. Then, 60 ml of toluene, 120 ml of heptane and 72 ml of water were added to the aqueous phase obtained above, the system was stirred for 30 minutes, and the organic phase was separated. 240 ml of water and 81 g of sodium chloride were then added to the aqueous phase and the product was extracted 3 times with toluene. The organic phases were combined and washed two times with a solution of 89 g of sodium chloride in 352 ml of water and then repeatedly with an aqueous solution of $H_2SO_4$ having a pH of 1.3. The final organic phase was washed with a 1% solution of $NaHCO_3$ in water, was concentrated to 176 ml under reduced pressure at 40° C. and 176 ml of heptane were added dropwise over a period of 1 hour. The suspension was stirred at 40° C. for at least 30 minutes, was cooled to 0° C. in at least 1.5 hours, is stirred for 1 hour, and filtered. The crude solid can be crystallized as in example 5.

Example 11

Crystallization of Anastrozole

First, 2.05 g of crude Anastrozole, obtained as in example 6 from toluene/heptane, were dissolved in 10.25 ml of toluene at 50° C. and 10.25 ml of heptane were added dropwise in 0.5 hours. The mixture was stirred at 50° C. for 20 minutes, was cooled to 22° C. in 2.5 hours, and maintained at the same temperature for 16 hours. The solid was filtered, washed twice with 20 ml of heptane, and dried at 55° C. under vacuum for 16 hours, yielding 1.88 g of product having HPLC purity as follows: Anastrozole 99.76%, Isoanastrozole 0.13%, other impurities 0.11%.

What is claimed:

1. A process for purifying Anastrozole of the following formula,

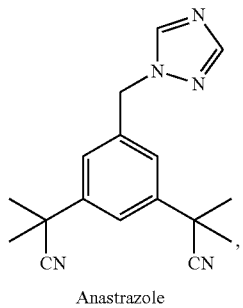

Anastrazole comprising the steps of:
a. extracting a quenched reaction mixture containing crude anastrazole with a mixture comprising toluene and a linear, branched or cyclic $C_{5-8}$ hydrocarbon and water to form an organic phase and an aqueous phase;
b. adding water to the aqueous phase;
c. extracting the aqueous phase formed in step (b) with toluene to produce an organic phase;
d. extracting the organic phase of step (c) with a polar mixture containing a solvent selected from the group consisting of N-methylpyrrolidinone (NMP) and a $C_{1-3}$ alcohol mixed with water, and
e. adding a linear, branched, or cyclic $C_{5-8}$ hydrocarbon to the organic phase of step (d) to precipitate Anastrozole.

2. The process of claim 1, further comprising preparing the Anastrozole in a process comprising the steps of:
a. combining 3,5-bis(2-cyanoisopropyl)toluene of formula I,

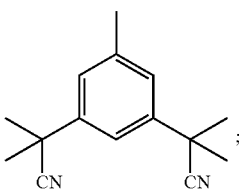

a solvent selected from the group consisting of acetonitrile (ACN), dichloromethane (DCM), and chlorobenzene; a brominating reagent selected from the group consisting of N-bromosuccinimide (NBS) and 1,3-dibromo-5,5-dimethyl-hydantoin; and 2,2'-azobis(2-methylpropionitrile);
b. heating the mixture; and
c. combining the heated mixture with 1,2,4-triazole; a solvent selected from the group consisting of NMP, dimethylformamide (DMF), mixtures of NMP and DMF, dimethylsulfoxide (DMSO), mixtures of DMSO and toluene, acetone, ACN, and tetrahydrofuran (THF); a base selected from the group consisting of NaOH, KOH, $K_2CO_3$, and $Na_2CO_3$ and 1,3-benzendiacetonitrile-5-(bromomethyl)-α,α,α,α-tetramethyl of formula II,

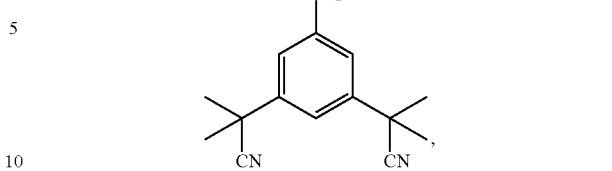

at a temperature below −20° C.

3. The process of claim 2, wherein step (a) comprises the following steps:
a. dissolving 3,5-bis (2-cyanoisopropyl)toluene of formula I in a solvent selected from the group consisting of ACN, DCM and chlorobenzene;
b. adding a brominating reagent selected from the group consisting of NBS and 1,3-dibromo-5,5-dimethylhydantoin to form a suspension;
c. maintaining the suspension at a temperature of about 20° C. to about 90° C. to form a solution;
d. combining the solution with 2,2'-azobis(2-methylpropionitrile), to form a reaction mixture;
e. heating the reaction mixture to a temperature of about 40° C. to about 95° C., providing 1,3-benzendiacetonitrile-5-(bromomethyl)-α,α,α,α-tetramethyl of formula II.

4. The process of claim 3, wherein the brominating reagent is NBS.

5. The process of claim 3, wherein the solvent is ACN.

6. The process of claim 5, wherein the solvent is ACN, and the suspension, in step b, is maintained at a temperature of about 65° C. to about 82° C.

7. The process of claim 3, wherein the solvent is chlorobenzene.

8. The process of claim 3, wherein the solvent is DCM.

9. The process of claim 3, wherein the reaction mixture is heated to a temperature of about 70° C. to about 82° C., in step e.

10. The process of claim 3, wherein the reaction mixture is heated for about 6 to about 12 hours, in step e.

11. The process of claim 10, wherein the reaction mixture is heated for about 6 to about 10 hours.

12. The process of claim 2, wherein step (c) comprises the following steps:
a. dissolving 1,2,4-triazole in a first solvent selected from the group consisting of NMP, DMF, mixtures of NMP and DMF, DMSO, mixtures of DMSO and toluene, acetone, ACN, and THF, at a temperature of about 20° C. to about 40° C.;
b. adding a base selected from the group consisting of NaOH, KOH, $K_2CO_3$, and $Na_2CO_3$, in a portion-wise manner, while maintaining the temperature below 40° C., to form a solution;
c. maintaining the solution for about 6 to about 18 hours;
d. cooling the solution to a temperature below −20° C.;
e. adding, slowly, a solution of 1,3-benzendiacetonitrile-5-(bromomethyl)-α,α,α,α-tetramethyl of formula II in a second solvent selected from the group consisting of NMP, DMF, mixtures of NMP and DMF, DMSO, mixtures of DMSO and toluene, acetone, ACN, and THF, while maintaining the temperature below −20° C., to form a reaction mixture;

f. maintaining the reaction mixture of step (e) for about 10 to about 20 hours, and g. quenching the reaction mixture formed in step (f).

13. The process of claim 12, wherein 1,2,4-triazole is dissolved, in step a, in the first solvent at a temperature of about 20° C. to about 35° C.

14. The process of claim 13, wherein the temperature is from about 20° C. to about 25° C.

15. The process of claim 12, wherein the first solvent is NMP.

16. The process of claim 12, wherein the base is NaOH.

17. The process of claim 12, wherein the base is added, in step b, over a period of about one to about one and half hours.

18. The process of claim 16, wherein during the addition of the base, the temperature is maintained at about 30° C. to about 60° C.

19. The process of claim 18, wherein the temperature is from about 30° C. to about 35° C.

20. The process of claim 12, wherein the solution is maintained for about 16 to about 20 hours.

21. The process of claim 12, wherein the solution is cooled, in step d, to a temperature of about −20° C. to about −30° C. prior to performing step e.

22. The process of claim 21, wherein the temperature is from about −20° C. to about −25° C.

23. The process of claim 12, wherein the 1,3-benzendiacetonitrile-5-(bromo-methyl)-α,α,α',α'-tetramethyl of formula II used, is a crude product obtained from bromination of a compound of formula I:

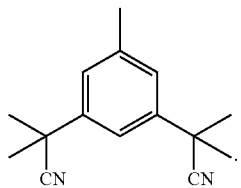

24. The process of claim 12, wherein the second solvent is the same as the first solvent.

25. The process of claim 12, wherein the addition performed in step e, is done over a period of about 4 to about 10 hours.

26. The process of claim 25, wherein the addition is done over a period of about 5 to about 7 hours.

27. The process of claim 12, wherein the reaction is maintained, in step f, for about 16 to about 20 hours.

28. The process of claim 17, wherein the reaction is maintained, in step f, at a temperature of less than −20° C.

29. The process of claim 28, wherein the temperature is from about −20° C. to about −30° C.

30. The process of claim 29, wherein the temperature is from about −20° C. to about −25° C.

31. The process of claim 12, wherein the progress of the reaction is monitored by HPLC.

32. The process of claim 12, wherein quenching is done by adding an organic acid.

33. The process of claim 32, wherein the organic acid is used in an amount sufficient to obtain a pH of about 6.5 to about 7.

34. The process of claim 33, wherein the organic acid is acetic acid.

35. The process according to claim 1, wherein prior to the extraction of the aqueous phase with toluene, an extraction of the aqueous phase using a mixture comprising toluene, a linear, branched or cyclic $C_{5-8}$ hydrocarbon and water, is done.

36. The process according to claim 1, wherein prior to adding the linear, branched, or cyclic $C_{5-8}$ hydrocarbon to precipitate Anastrozole, the reaction mixture is concentrated.

37. The process of claim 36, wherein the reaction mixture is concentrated under reduced pressure.

38. The process according to claim 1, wherein the linear, branched, or cyclic $C_{5-8}$ hydrocarbon is added drop-wise to the concentrated reaction mixture.

39. The process of claim 38, wherein the addition is done over a period of about 1 to about 1.5 hours, providing a suspension.

40. The process of claim 39, wherein the suspension is cooled to a temperature of about 10 to about 0° C., prior to collecting the precipitate.

41. The process of claim 40, wherein the suspension is cooled to a temperature of about 5° C. to about 0° C., prior to collecting the precipitate.

42. The process of claim 41, wherein the precipitate is collected and dried.

43. The process according to claim 1, wherein the linear, branched, or cyclic $C_{5-8}$ hydrocarbon is hexane, heptane, or cyclohexane.

44. The process of claim 43, wherein the linear, branched or cyclic $C_{5-8}$ hydro-carbon is heptane.

45. The process according to claim 1, wherein the $C_{1-3}$ alcohol is methanol.

46. The process according to claim 1, wherein the polar mixture contains methanol and water.

47. The process of claim 1, further comprising crystallization of Anastrozole.

48. The process of claim 47, wherein the crystallization is from a mixture of a solvent and an anti-solvent; wherein the solvent is selected from the group consisting of acetone, ethanol, 2-propanol, methanol, DCM, n-butanol, ACN, ethylacetate and toluene, and the anti-solvent is selected from the group consisting of heptane, DIPE, water, and cyclohexane.

49. The process of claim 48, wherein the mixtures of a solvent and an anti-solvent are selected from the group consisting of acetone and heptane, ethanol and heptane, ethanol and DIPE, ethanol and water, methanol and water, DCM and DIPE, 2-propanol and heptane, n-butanol and heptane, 2-propanol and DIPE, 2-propanol and water, n-butanol and DIPE, ACN and water, 2-propanol and heptane, and toluene and heptane.

50. The process of claim 49, wherein the mixtures of a solvent and an anti-solvent are selected from the group consisting of 2-propanol and heptane, toluene and heptane, and methanol and water.

51. The process of claim 48, wherein the crystallization is done by the following steps:

a. dissolving Anastrozole in the solvent;

b. adding, in a drop-wise manner, the anti-solvent, and c. cooling to a temperature of about 10° C. to about 0° C.

52. The process of claim 51, wherein the Anastrozole in step a is crude Anastrozole.

53. The process of claim 52, wherein crude Anastrozole contains at least one of the impurities: Isoanastrozole, 3,5-bis(2-cyanoisopropyl)toluene, 1,1-dibromomethyl-3,5-bis(2-cyanoisopropyl)benzene and other impurities.

54. The process of claim 51, wherein the dissolution is done by heating Anastrozole and the solvent to a temperature of about 20° C. to about 55° C.

55. The process of claim 51, wherein the solvent is methanol, 2-propanol, or toluene.

56. The process of claim 55, wherein the solvent is methanol.

57. The process of claim 51, wherein the Anastrozole is dissolved in the solvent at a temperature of about 20° C. to about 30° C.

58. The process of claim 57, wherein the temperature is of about 20° C. to about 25° C.

59. The process of claim 51, wherein the solvent is 2-propanol or toluene.

60. The process of claim 51, wherein the temperature range is from about 40° C. to about 50° C.

61. The process of claim 51, wherein the anti-solvent is heptane or water.

62. The process claim 51, wherein the anti-solvent is heptane and the solvent is 2-propanol or toluene.

63. The process of claim 51, wherein the anti-solvent is added slowly.

64. The process of claim 51, wherein the anti-solvent is added over a period of about 15 minutes to about 2 hours.

65. The process of claim 51, wherein the addition is done over a period of about 0.5 an hour to about 2 hours.

66. The process of claim 65, wherein the addition is done over a period of about an hour to about 1.2 hours.

67. The process claim 51, wherein the anti-solvent is water and the solvent is methanol.

68. The process of claim 51, wherein the addition is done over a period of about 1 hour to about 2 hours.

69. The process of claim 68, wherein the addition is done over a period of about 75 to about 100 minutes.

70. The process of claim 51, wherein the anti-solvent is added under stirring.

71. The process of claim 51, wherein a suspension is obtained at the end of the addition of the anti-solvent.

72. The process of claim 51, wherein the suspension is cooled to a temperature of about 5° C. to about 0° C.

73. The process of claim 51, wherein the temperature is from about 2° C. to about 0° C.

74. The process of claim 72, wherein cooling is done over a period of about 1 to about 2 hours.

75. The process of claim 72, wherein cooling is done over a period of about 75 to about 100 minutes.

76. The process of claim 51, further comprising maintaining the suspension for about 1 hour to about 2 hours.

77. The process of claim 76, wherein the suspension is maintained for about 1.5 to about 2 hours 78. The process of claim 76, wherein the suspension is maintained for about 90 to about 100 minutes.

79. The process of claim 1, further comprising preparing the Anastrozole in a process comprising the steps of:

a. preparing a derivative of 3,5-bis(2-cyanoisopropyl)toluene of formula I,

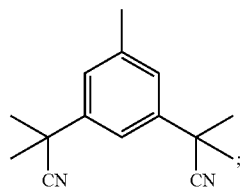

wherein the derivative contains a leaving group other than bromine, but in the same structural position as the bromine in the structure of formula II:

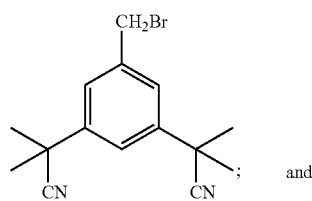

b. reacting the derivative formed in step (a) with 1,2,4-triazole and a base selected from the group consisting of NaOH, KOH, $K_2CO_3$, and $Na_2CO_3$ at a temperature below −20° C.

80. The process according to claim 79, wherein the leaving group other than bromine is selected from the group consisting of Cl, I, methanesulfonate and toluenesulfonate.

* * * * *